(12) United States Patent
Jäger et al.

(10) Patent No.: US 10,290,373 B2
(45) Date of Patent: May 14, 2019

(54) PATIENT COUCH WITH A CONTROL SYSTEM AND METHOD FOR CONTROLLING THE PATIENT COUCH

(71) Applicants: Anja Jäger, Fürth (DE); Robert Kagermeier, Nürnberg (DE)

(72) Inventors: Anja Jäger, Fürth (DE); Robert Kagermeier, Nürnberg (DE)

(73) Assignee: Siemens Aktiengesellschaft, München (DE)

( * ) Notice: Subject to any disclaimer, the term of this patent is extended or adjusted under 35 U.S.C. 154(b) by 495 days.

(21) Appl. No.: 14/705,676

(22) Filed: May 6, 2015

(65) Prior Publication Data

US 2015/0320369 A1    Nov. 12, 2015

(30) Foreign Application Priority Data

May 6, 2014 (DE) ........................ 10 2014 208 463

(51) Int. Cl.
*A61B 6/00* (2006.01)
*A61B 6/03* (2006.01)
(Continued)

(52) U.S. Cl.
CPC ........... *G16H 40/63* (2018.01); *A61B 5/0555* (2013.01); *A61B 6/035* (2013.01); *A61B 6/0407* (2013.01);
(Continued)

(58) Field of Classification Search
CPC ..................... G06F 3/017; G06F 3/005; G06K 9/00335–9/00338; G06T 2207/10028
See application file for complete search history.

(56) References Cited

U.S. PATENT DOCUMENTS

| 6,677,969 B1 | 1/2004 | Hongo |
| 2005/0025706 A1 | 2/2005 | Kagermeier |

(Continued)

FOREIGN PATENT DOCUMENTS

| CN | 101119680 A | 2/2008 |
| CN | 101889870 A | 11/2010 |

(Continued)

OTHER PUBLICATIONS

Caon, Maurizio, et al. "Context-aware 3d gesture interaction based on multiple kinects." Proceedings of the first international conference on ambient computing, applications, services and technologies, Ambient. 2011.*

(Continued)

*Primary Examiner* — Vincent Rudolph
*Assistant Examiner* — Raphael Schwartz
(74) *Attorney, Agent, or Firm* — Lempia Summerfield Katz LLC

(57) ABSTRACT

A patient couch with a control system and a method for controlling the patient couch are provided. The control system is based on a three-dimensional (3D) camera for recording first 3D images of a recording area. The 3D camera is attached to the patient couch. An image processing unit for identifying at least one control gesture in the first 3D images allows a safe and fast control of the x-ray device. In order to carry out the control, the control system includes a control unit with a motor for controlling a movement of the patient couch based on the first control gesture.

6 Claims, 2 Drawing Sheets

(51) Int. Cl.
    *A61B 6/04*     (2006.01)
    *A61B 5/055*     (2006.01)
    *A61G 7/018*     (2006.01)
    *G05B 15/02*     (2006.01)
    *G06F 19/00*     (2018.01)
    *G16H 40/63*     (2018.01)

(52) U.S. Cl.
    CPC .......... *A61B 6/0457* (2013.01); *A61B 6/4441* (2013.01); *A61G 7/018* (2013.01); *G05B 15/02* (2013.01); *G06F 19/00* (2013.01); *A61G 2203/10* (2013.01); *A61G 2203/22* (2013.01)

(56) References Cited

U.S. PATENT DOCUMENTS

| | | | |
|---|---|---|---|
| 2010/0104134 A1* | 4/2010 | Wang | G06F 3/0304 382/103 |
| 2011/0286579 A1 | 11/2011 | Butzine et al. | |
| 2012/0051521 A1 | 3/2012 | Nishino | |
| 2012/0290121 A1 | 11/2012 | Gronbach | |
| 2013/0205501 A1 | 8/2013 | Robertson et al. | |
| 2013/0342851 A1 | 12/2013 | Dresel et al. | |
| 2014/0090171 A1 | 4/2014 | Hyde et al. | |

FOREIGN PATENT DOCUMENTS

| | | |
|---|---|---|
| CN | 102258374 A | 11/2011 |
| CN | 102270035 A | 12/2011 |
| CN | 102415892 A | 4/2012 |
| CN | 102778858 A | 11/2012 |
| DE | 19627659 C1 | 1/1998 |
| DE | 10334073 A1 | 2/2005 |
| DE | 102012205549 A1 | 10/2013 |
| DE | 102012209190 A1 | 12/2013 |

OTHER PUBLICATIONS

Chinese Office Action for Chinese Patent Application No. 201510186333.2, dated Jan. 26, 2017, with English Abstract.
German Office Action for German Application No. 10 2014 208 463.6, dated Nov. 18, 2014 with English Translation.

* cited by examiner

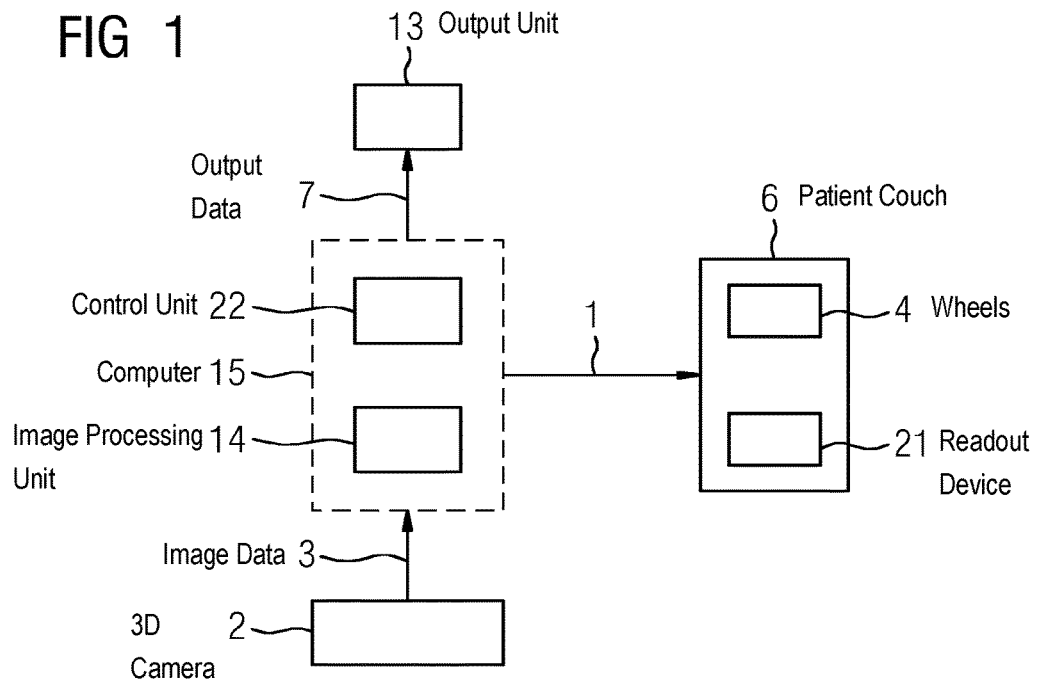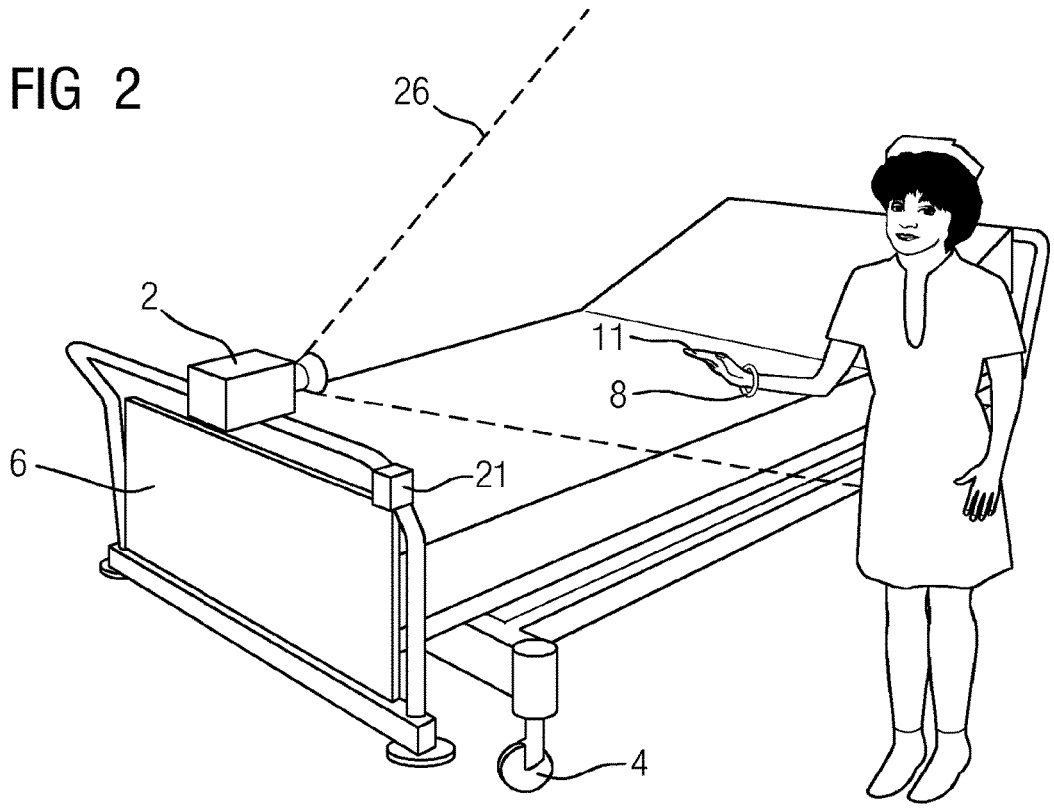

PATIENT COUCH WITH A CONTROL SYSTEM AND METHOD FOR CONTROLLING THE PATIENT COUCH

This application claims the benefit of DE 10 2014 208 463.6, filed on May 6, 2014, which is hereby incorporated by reference in its entirety.

BACKGROUND

In the medical environment, it is important to be able to control devices safely and quickly and also as hygienically as possible. Conventionally, operating elements such as pushbuttons, switches or levers are used for control of a device in the medical environment. Control by such operating elements is frequently less intuitive, which provides that control may become uncertain by virtue of possible errors during operation. Less intuitive operation frequently provides less rapid operation, since the user of the device to be operated is to first understand the function of the individual operating elements. The cleaning of such operating elements in the clinical environment is complex, or the operating elements are covered with sterile film. This makes it expensive to guarantee the required hygiene of conventional control systems.

Innovative concepts for controlling medical devices are based on the recognition of gestures of the user using a 3D camera. For example, non-contact operation is provided, and thereby, hygienic control of a medical device is provided. In publication DE 10 2012 205 549 A1, the improved control of a dead man's handle in a non-contact controlled medical device is described. In this case, a gesture-based request signal is projected as a light signal into an operating area. In response, an answer signal in the form of a gesture is detected by automatic gesture recognition. The response signal is evaluated in a computer and is used for controlling a switch.

SUMMARY AND DESCRIPTION

The scope of the present invention is defined solely by the appended claims and is not affected to any degree by the statements within this summary.

The present embodiments may obviate one or more of the drawbacks or limitations in the related art. For example, safe and rapid control of a patient couch as well as a corresponding control system are provided. The control system is easy to clean, and control is as hygienic as possible.

An apparatus and a method are provided. Features and advantages or alternate forms of embodiments mentioned here for one type of subject matter are likewise also to be transferred to the other subject matter and vice versa. In other words, the apparatus may be further developed with the features that are described in conjunction with the method. The corresponding functional features of the method are embodied by corresponding physical modules.

The present embodiments relate to a patient couch with a control system as well as to a method for controlling a patient couch. The control system is based on a 3D camera to record first 3D images of a recording area. The 3D camera is attached to a patient couch. An image processing unit for identifying at least one control gesture in the first 3D images allows safe and rapid control of the x-ray device. In order to undertake the control, the control system includes a control unit with a motor for controlling a movement of the patient couch based on the first control gesture. The risk of incorrect operation is reduced by one or more of the present embodiments since the user may control the patient couch very easily and intuitively. The non-contact control of the patient couch provides that the control system is also extremely hygienic.

In accordance with a further aspect, the patient couch has wheels on a floor side of the patient couch. The control unit is configured to control the movement of the patient couch by the wheels. This provides that the patient couch is embodied to be especially mobile and may be used for transport of the patient.

In accordance with a further aspect, the control unit is configured to control a translation movement and/or a rotation movement of the patient couch. This provides that the control of the patient couch is configured especially flexibly.

In accordance with a further aspect, the control system includes a readout device. The readout device is configured for reading out an authorization signal in the immediate vicinity of the patient couch. The control system is configured for enabling the control unit based on the authorization signal. This provides that it is only possible for authorized users to control the patient couch, so that safety is enhanced during control.

In accordance with a further aspect, the control system includes a second 3D camera attached to the transport apparatus for recording second 3D images of the recording area. The image processing unit is configured for identifying at least one second control gesture in the second 3D images and also for comparing the identified first and second control gesture. The control unit is configured to control a movement of the patient couch based on the result of the comparison. This enhances the reliability of the control of the patient couch.

BRIEF DESCRIPTION OF THE DRAWINGS

FIG. 1 shows one embodiment of a patient couch with control system;

FIG. 2 shows one embodiment of a patient couch with control system; and

DETAILED DESCRIPTION

Figure 3:
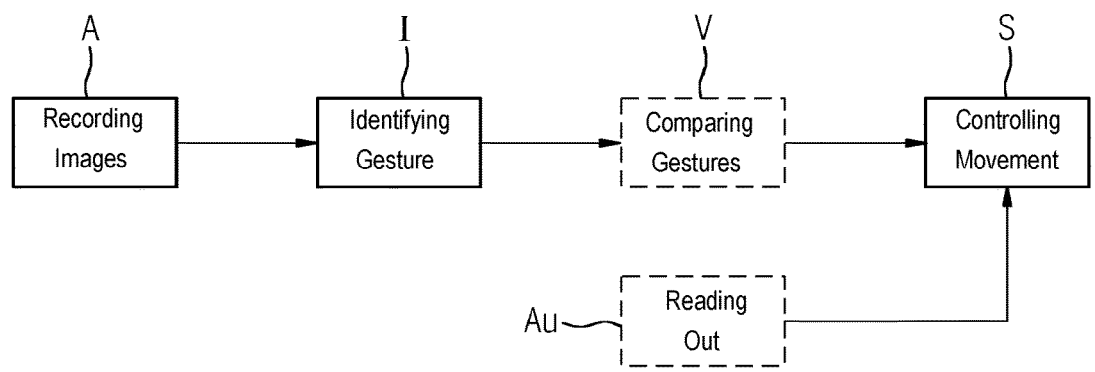
FIG. 3 shows a flow diagram of one embodiment of a method.

FIG. 1 shows one embodiment of a patient couch with a control system. A patient couch 6 may be a couch that is suitable for supporting a patient. For example, the patient couch 6 may be a patient couch 6 for supporting a patient during diagnostic imaging using an imaging device, such as a C-arm x-ray device or a tomography device. A tomography device may, for example, include a computed tomograph or a magnetic resonance tomograph. Such a patient couch 6 may be installed fixed by a couch base, so that the position of the patient couch 6 is controlled relative to the imaging device. For example, the patient couch 6 may be moved relative to a system axis of the imaging device. The height of the patient couch 6 may be controlled. In an embodiment, the patient couch 6 may be movable freely in the room by wheels mounted on a floor side of the patient couch 6, for example.

In this case, a 3D camera 2 is fastened to the patient couch 6. The 3D camera 2 is configured to record 3D images of a recording area 26. A 3D camera 2 may be a camera that may record images with spatial depth information. The 3D camera 2 is configured for detection of electromagnetic radiation (e.g., for detection of electromagnetic radiation in a spectrum at a lower frequency compared to x-ray radiation, such as in the visible or infrared spectrum). The 3D camera 2 is embodied as a stereo camera or as a time-of-flight camera, for example. In a further embodiment, the 3D camera is embodied for scanning the recording area 26 by structured illumination.

The control system also includes an image processing unit 14 that may be embodied both in the form of hardware and also of software. The 3D images are forwarded as image data 3 from the 3D camera 2 to the image processing unit 14. The image processing unit 14 identifies at least one control gesture in the 3D images. A control gesture involves a defined sequence of individual movement steps of the input element 11. For example, a control gesture may be identified based on movement steps of individual components of the input element 11 or over a number of input elements 11. If the input element 11 involves a hand, a control gesture may, for example, be identified through the movement of the hand as a whole and/or through a relative movement of individual fingers in relation to one another. The control gesture may be a defined sequence of movement steps of two hands in relation to one another.

An input element 11 includes a material object that has a suitable size and suitable optical characteristics to enable the material object to be identified in a 3D image. For example, an input element 11 may include a bodily object such as a finger, a hand or a foot. In one embodiment, an input element 11 may also include an object highlighted by color and/or geometry of the object (e.g., a fluorescent object or a stick-shaped object). The input element 11 may be determined in the 3D images segmented and/or by pattern recognition (e.g., in order to support the identification of the control gesture). Such a segmentation and/or pattern recognition may be undertaken by the image processing unit 14.

A control gesture is identified precisely since the 3D images provide depth information. This also makes it possible to determine the position of the input element 11 precisely in space. Therefore, the control gesture may also be identified in relation to a specific position and/or orientation in space. Thus, the image processing unit 14 may be configured to detect an optical marker in space or on the patient couch 6 and to determine the position and/or orientation of the input element from the markers. The optical markers may include, for example, at least three optical markers not lying in one plane. Optical marker sources are of visible light or infrared radiation, for example.

The image processing unit 14 is configured to communicate with the control unit 22 (e.g., to signal the identified control gesture to the control unit 22). The control system has a control unit 22 configured to control a movement of the patient couch 6 based on a control gesture. The couch may, for example, be controlled by the motor. The control unit 22 computes, with hardware or software, at least one control signal 1. The control signal 1 may be transmitted to the respective unit to be controlled (e.g., to a motor) both by wire and also wirelessly.

The control system may be connected to a computer 15 or may include the computer 15. The computer 15, in the form of embodiment shown here, has further interfaces to enable the computer 15 to communicate with the output unit 13. The interface includes generally-known hardware or software interfaces (e.g., the hardware interfaces PCI bus, USB or Firewire). The computer 15 is connected to an output unit 13, for transmission of output data 7, for example. The output unit 13 includes one or more LCD, plasma or OLED screen(s). The computer 15 may be connected to an additional input unit.

The computer 15 is configured to load a computer program into an internal memory. The computer program includes instructions that are readable by the computer 15. The instructions of the computer program readable by the computer 15 are configured to control the method of one or more of the present embodiments when the instructions are executed on the computer 15. In further embodiments, both the computer program and also the control unit 22 are configured to access information obtained from 3D images taken by the 3D camera 2 and to create a control signal 1 for controlling the movement of the patient couch 6. The computer program may be stored on a computer-readable medium. The computer-readable medium may, for example, also include a DVD, a USB stick, a hard disk or a diskette.

The patient couch 6 may be moved immediately after the identification of the control gesture, so that the user experiences feedback to the control gesture that the user has made without any perceptible time lag. The feedback includes, for example, the movement of the patient couch. For example, in this way, continuous control that is undertaken safely, precisely and quickly may be made possible. For example, a continuous movement of the hand may cause a continuous movement of the patient couch 6.

The authorization of the user may be checked (e.g., by a readout device 21 for reading out an authorization signal attached to the patient couch 6). The authorization signal is provided, for example, by a barcode, Radio-Frequency Identification (RFID) or Near Field Communication (NFC). The information may be read out optically or by radio communication. A person may prove themselves as authorized by carrying a signal generator 8 with them (e.g., in the form of an RFID chip or an NFC chip or an optically-readable barcode). Such a signal generator 8 may be integrated into wearable units, such as an armband, for example, or may be integrated into a smartcard. The control is thus only enabled when an authorized person with a corresponding signal generator 8 is close enough to the readout device 21 attached to the patient couch 6 or places the signal generator 8 in such a way for providing the authorization signal that the authorization signal may be read out by the readout device 21. In this way, control of the patient couch 6 by a non-authorized person is prevented.

In the embodiment shown in FIG. 2, the patient couch 6 has wheels 4 on a floor side of the patient couch 6. The control unit 22 is configured to control the movement of the patient couch 6 by the wheels 4. This provides that the control unit 22 is, for example, configured for controlling a translation movement and/or a rotation movement of the patient couch 6. The control system, however, may also make it possible to control the height of the patient couch 6 or to control the support of the patient by adjusting the frame of the patient couch 6.

The 3D camera 2 may be fastened pivotably to the patient couch 6. By pivoting the 3D camera 2, the recording area 26 may be modified, through which the control system as a whole may be more flexibly configured. For example, automatic pivoting of the 3D camera 2, such that the recording area 26 follows a moving input element 11, may be provided. This also provides, for a continuous movement of the input element 11, that the element lies in the recording area 26 of the 3D camera 2. This is of advantage, for example, if a continuous movement of the patient couch 6 is to be controlled with the control unit (e.g., for moving the patient couch 6 over distances of the order of magnitude of the patient couch 6).

FIG. 3 shows a flow diagram of one embodiment of a method. The method includes recording A first 3D images of a recording area 26 using a first 3D camera 2, identifying I at least one first control gesture in the first 3D images 2, and controlling S a movement of the patient couch by the control unit 22 based on the first control gesture. Another embodiment includes recording A second 3D images of the recording area using a second 3D camera 2, identifying I at least one second control gesture in the second 3D images, comparing V the identified first and second control gesture, and controlling S a movement of the patient couch 6 by the control unit 22 based on the result of the comparison. The method of one or more of the present embodiments may include reading out Au an authorization signal in the immediate vicinity of the patient couch 6 and controlling S a movement of the patient couch 6 by the control unit 22 based on the authorization signal.

In order to improve the safety during the control of the patient couch 6, in one embodiment, a mechanism for enabling the control may be provided. The patient couch 6 is controlled only after a corresponding enabling. For example, a switch may be placed in the vicinity or directly on the patient couch 6. Actuating the switch causes the control to be enabled. In addition, further mechanisms for enhancing safety may also be provided. Thus, a laser barrier may be installed in the recording area 26 of the 3D camera 2. Interrupting the laser barrier may lead to enabling. By an appropriate positioning of the laser barrier (e.g., above the patient couch 6), it may be provided that an input element 11 is detected in a predetermined plane. Also, a second 3D camera 2 for recording the second 3D images may be employed. This enables a second control gesture to be identified in the second 3D images. A comparison of two control gestures established independently of one another increases the safety of the control. A speech command may be used to enable control. The enabling may also be restricted only for a specific period of time. Thus, in the embodiment, if no control gesture is recognized in the 3D images within a specific period of time after the enabling, then control of the x-ray device is no longer possible, at least without renewed enabling.

A mechanism for stopping the movement may also be provided for controlling the patient couch 6. Such a mechanism likewise enhances the safety of the control. For example, the mechanism may be triggered by a patient supported on the patient couch 6 and also by a user of the control system. For example, the mechanism is triggered by actuating a button or a switch. As an alternative, the mechanism may be triggered by making a specific control gesture.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A patient couch comprising:
a control system comprising:
a first three-dimensional (3D) camera attached to the patient couch, the first 3D camera operable to record first 3D images of a recording area;
an image processing unit configured to determine an input element in the first 3D images and identify at least one first control gesture based on the input element in the first 3D images; and
a control unit comprising a motor, the motor operable to control a movement of the patient couch based on the at least one first control gesture,
wherein the control system further comprises a second 3D camera attached to the patient couch, the second 3D camera operable to record second 3D images of the recording area,
wherein the image processing unit is further configured to:
determine the input element in the second 3D images
identify at least one second control gesture based on the input element in the second 3D images, independent of the identification of the first control gesture in the first 3D images; and
compare the at least one identified first control gesture and the at least one identified second control gesture,
wherein the control unit is configured to control a movement of the patient couch based on a result of the comparison, and
wherein the first 3D camera is pivotably mounted to the patient couch and configured to automatically pivot to follow the input element, such that the recording area is modified.

2. The patient couch of claim 1, wherein the patient couch further comprises wheels on a floor side, and
wherein the control unit is configured to control the movement of the patient couch using the wheels.

3. The patient couch of claim 2, wherein the control unit is configured to control a translation movement, a rotation movement, or the translation movement and the rotation movement of the patient couch.

4. A method for controlling a patient couch, the method comprising:
recording first three-dimensional (3D) images of a recording area using a first 3D camera, wherein the first 3D camera is pivotably mounted to the patient couch;
determining an input element in the first 3D images;
identifying at least one first control gesture based on the input element in the first 3D images;
controlling, by a controller, a movement of the patient couch based on the at least one first control gesture;
recording second 3D images of the recording area using a second 3D camera;
determining the input element in the second 3D images;
identifying at least one second control gesture based on the input element in the second 3D images, independent of the identification of the first control gesture in the first 3D images;
comparing the at least one identified first control gesture and the at least one second control gesture;
controlling, by the controller, a movement of the patient couch based on a result of the comparison; and
modifying the recording area, the modifying of the recording area comprising automatically pivoting the first 3D camera to follow the input element.

5. The method of claim 4, further comprising controlling a translation movement, a rotation movement, or the translation movement and the rotation movement of the patient couch.

6. The method of claim 4, further comprising:
reading-out an authorization signal in the immediate vicinity of the patient couch; and
controlling, by the controller, a movement of the patient couch based on the authorization signal.

* * * * *